(12) United States Patent
Camden

(10) Patent No.: US 6,329,355 B1
(45) Date of Patent: Dec. 11, 2001

(54) METHOD FOR INHIBITING THE GROWTH OF CANCERS

(75) Inventor: James Berger Camden, Weat Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/552,408

(22) Filed: Apr. 19, 2000

Related U.S. Application Data

(62) Division of application No. 09/218,884, filed on Dec. 22, 1998, which is a division of application No. 08/788,482, filed on Jan. 28, 1997, now Pat. No. 5,900,429.

(51) Int. Cl.$^7$ .......................... A61K 31/66; A61K 31/44; A61K 31/415
(52) U.S. Cl. .......................... 514/110; 514/343; 514/388; 514/395
(58) Field of Search .................................. 514/110, 343, 514/388, 395

(56) References Cited

U.S. PATENT DOCUMENTS

| | | | |
|---|---|---|---|
| 3,010,968 | 11/1961 | Loux .................. | 260/309.2 |
| 3,370,957 | 2/1968 | Wagner et al. .......... | 99/90 |
| 3,499,761 | 3/1970 | Dersch . | |
| 3,541,213 | 11/1970 | Klopping .............. | 424/273 |
| 3,669,969 | 6/1972 | Lunn .................. | 260/256.4 |
| 3,738,995 | 6/1973 | Adams et al. .......... | 260/309.2 |
| 3,881,014 | 4/1975 | Regel et al. .......... | 424/273 |
| 3,956,262 | 5/1976 | Heyes et al. .......... | 260/140 |
| 4,046,906 | 9/1977 | Frensch et al. ........ | 424/273 |
| 4,731,366 | 3/1988 | Munro et al. .......... | 514/278 |
| 4,814,329 | 3/1989 | Harsanyi et al. ....... | 514/396 |
| 5,098,923 | 3/1992 | Karjalainen et al. .... | 514/396 |
| 5,114,951 | 5/1992 | King .................. | 514/290 |
| 5,149,527 | 9/1992 | Weisenthal . | |
| 5,290,801 | 3/1994 | Higley et al. ......... | 514/395 |
| 5,310,748 | 5/1994 | Wilde et al. .......... | 514/395 |
| 5,329,012 | 7/1994 | Anderson .............. | 548/318.5 |
| 5,364,875 | 11/1994 | Wilde ................. | 514/375 |
| 5,434,163 | 7/1995 | Edlind et al. ......... | 514/310 |
| 5,629,341 | 5/1997 | Camden . | |
| 5,656,615 | 8/1997 | Camden . | |
| 5,665,713 | 9/1997 | Camden . | |
| 5,665,751 | 9/1997 | Camden . | |
| 5,767,138 | 6/1998 | Camden . | |
| 5,770,616 | 6/1998 | Camden . | |
| 5,840,742 | 11/1998 | Camden . | |
| 5,854,231 | 12/1998 | Camden . | |
| 5,872,142 | 2/1999 | Camden . | |
| 5,880,144 | 3/1999 | Camden . | |
| 5,900,429 | 5/1999 | Camden . | |
| 5,902,804 | 5/1999 | Camden . | |
| 5,908,855 | 6/1999 | Camden . | |
| 5,929,099 | 7/1999 | Camden . | |
| 5,932,604 | 8/1999 | Camden . | |
| 5,932,609 | 8/1999 | Camden . | |
| 6,025,377 | 2/2000 | Camden . | |
| 6,077,862 | 6/2000 | Camden . | |

FOREIGN PATENT DOCUMENTS

| | | |
|---|---|---|
| 667158 | 11/1965 | (BE) . |
| 617968 | 10/1994 | (EP) . |
| 2155888 | 5/1973 | (FR) . |
| 07 277 956 | 10/1995 | (JP) . |
| WO 94/04541 | 3/1994 | (WO) . |
| WO 96/32103 | 10/1996 | (WO) . |
| WO 96/32104 | 10/1996 | (WO) . |
| WO 96/32107 | 10/1996 | (WO) . |
| WO 96/32115 | 10/1996 | (WO) . |
| WO 96/40120 | 12/1996 | (WO) . |
| WO 96/40122 | 12/1996 | (WO) . |
| Wo 96/40119 | 12/1996 | (WO) . |
| WO 97/05870 | 2/1997 | (WO) . |
| WO 97/05872 | 2/1997 | (WO) . |
| WO 97/05873 | 2/1997 | (WO) . |
| WO 98/32440 | 2/1998 | (WO) . |
| WO 98/51303 | 11/1998 | (WO) . |
| WO 98/51304 | 11/1998 | (WO) . |
| WO 99/59585 | 11/1999 | (WO) . |

OTHER PUBLICATIONS

Lapras, M. et al. Bull. Soc. Sci. Vet. et Med. comparee, Lyon, 1975, vol. 77, No. 6, pp. 379–397 (in French)—and English translation thereof.

Chemical Abstracts 65:6570h referring to BE patent, date unknown (1995).

Elgebaly et al., J. Natl. Cancer Inst., vol. 74, No. 4, pp. 811–815 (1985).

Friedman, et al., Biochemica et Biophysica Acta, 544 (1978) pp. 605–614.

Lacey, et al., Biochemical Pharama, vol. 34, No. 19, pp. 3603–3605 (1985).

Chemical Abstracts 121:175012z, (1994) p 607, Katiyar, et al.

Stedman's Medical Dictionary, 24$^{th}$ ed., 1983, pp./ 777/778.

Aur, J. Pediatr., 78, No. 1, (1971) pp. 129–131.

Lundy et al., Cancer Treat. Rep., vol. 62, No. 11, (1978), pp. 1955–1962.

(List continued on next page.)

Primary Examiner—Jerome D. Goldberg
(74) Attorney, Agent, or Firm—Rose Ann Dabek; Bart S. Hersko

(57) ABSTRACT

A method for inhibiting the growth of tumors and cancers in mammals comprising administering a chemotherapeutic agent to significantly reduce the tumor in mass and then administering a benzimidazole derivative. Potentiators can also be included in the benzimidazole composition.

12 Claims, No Drawings

OTHER PUBLICATIONS

Lundy et al., Surg. Forum, vol. 27, No. 62 (1976) pp. 132–134.
Marinovich, et al., Toxicol., vol. 94, No. 1–3, (1994) pp. 173–185.
Lovett, Diss. Abstr. Int., (Sci), vol. 39, No. 11, (1979) pp. 5315–5316.
Brabender, et al., Cancer Research, vol. 36 (Mar. 1976) pp. 905–916.
Atassi et al., Europ., J. Cancer, vol. 11 (1975) pp. 599–607.
Brown, et al., J. Am. Chem. Soc., 83:1764–65 (1961).
Grenda, et al., J. Org. Chem. 30,259 (1965).
W.T. Thompson, Agricultural Chemicals Book IV, Fungicides, pp. 154, 121, 123 (1993–1997).
Carter, W.A. CRC Press, Selective Inhibitors of Viral Functions, pp. 277–346 (1975).
Merck Index, Eighth Edition, 1968, p. 1035.
DuPont, Material Safety Data Sheet Benlate Fungicide, Sep. 27, 1994.
Derwent Publications, AN 95–400884 and Japan Patent Abstracts, JP 07 277956 (duplicate of JP cited supra) (1995).
Teicher, et al., Breast Cancer Research and Treatment, vol. 36, No. 2, pp. 227–236 (1995).
Bissery, et al., Seminars in Oncology: Management of Breast Cancer: A New Therapeutic Approach, vol. 22, No. 6–S13, pp. 3–16, (1995).
Chemical Abstracts 113:112365 (1990) Ghannoun, et al.
Ram, et al., J. Med. Chem., 35, No. 3, 539–547 (1992).
Nene, et al., International Science Publisher, Fungicides in Plant Disease Control, Chapter 9, 1993.
Private Communication to Dr. Von Hoff from National Institute of Health, National Cancer Society (1995).
Chemical Abstracts 92:123231 (1979) Menzel et al.
Lacey et al., International Journal for Parasitology, vol. 18 No. 7, pp 885–936 (1988).
Merck Index, 12$^{th}$ ed., 7943 and 9877, Merck & Co. (NJ 1996).
Chemical Abstracts 102:217569 (1985) Elgebaly et al.
Chemical Abstracts 87:161659 (1957) Lundy et al.
Lacey, et al., Biochemical Pharma., vol. 34, No. 7, pp. 1073–1077 (1985).
Lassnau, et al., Chest, vol. 104, pp 119–122 (1993).
Georgopapadakov et al., Science vol. 264, pp. 371–373 (Apr. 15, 1994).
Carter et al., Chemotherapy of Cancer, 2$^{nd}$ Ed., John Wiley & Sons, NY, NY (1981), pp. 362–365.
Pending Application of Camden, Serial No. 09/371,457, filed Aug. 10, 1999. (5784R).
Pending Application of Camden, Serial No. 09/371,459, filed Aug. 10, 1999. (5784R2).
Pending Application of Camden, Serial No. 09/364,021, filed Jul. 30, 1999. (5785D2).
Pending Application of Camden, Serial No. 09/408,664, filed Sep. 29, 1999. (5785D2R).
Pending Application of Camden, Serial No. 09/312,948, filed May 18, 1999. (5786D).
Pending Application of Camden, Serial No. 09/394, 383, filed Sep. 10, 1999. (5786DR).
Pending Application of Camden, Serial No. 09/394,382, filed Sep. 10, 1999. (5786DR2).
Pending Application of Camden, Serial No. 09/218,884, filed Dec. 22, 1998. (6496D).
Pending Application of Camden, Serial No. 08/857,811, filed May 16, 1997, CPA filed Jul. 28, 1999. (6643).
Pending Application of Camden, Serial No. 09/312,949, filed May 17, 1999. (7161R).
Pending Application of Camden, Serial No. 09/374,717, filed Aug. 13, 1999. (7719).
Pending Application of Camden, Serial No. 09/552,408, filed Apr. 19, 2000. (6496D2).
Pending Application of Camden, Serial No. 09/552,852, filed Apr. 20, 2000. (6643D2).
Pending Application of Camden, Serial No. 09/552,820, filed Apr. 20, 2000. (6643D3).
Pending Application of Camden, Serial No. 09/560,059, filed Apr. 27, 2000. (5781D3).
Pending Application of Camden, Serial No. 09/603,040, filed Jun. 26, 2000. (5781DC).
Pending Application of Camden, Serial No. Not Yet Correctly Assigned, Assigned same SN as 8069, filed Apr. 28, 2000. (8068).
Pending Application of Camden, Serial No. Not Yet Correctly Assigned, Assigned same SN as 8068, filed Apr. 28, 2000. (8069).
Pending Application of Camden, Serial No. 09/602,170, filed Jun. 22, 2000. (5783C2).
Pending Application of Camden, Serial No. 09/603,322, filed Jun. 26, 2000. (5781D2).

METHOD FOR INHIBITING THE GROWTH OF CANCERS

This is a divisional application of copending application Ser. No. 09/218,884, filed Dec. 22, 1998, which is a division of application Ser. No. 08/788,482, filed Jan. 28, 1997, now U.S. Pat. No. 5,900,429; the disclosures of which are incorporated herein by reference.

TECHNICAL FIELD

This invention is a method of inhibiting the growth of cancers and tumors in mammals, particularly in human and warm blooded animals. The method involves the sequential administration of chemotherapeutic agents which reduce the tumor size and a benzimidazole derivative, preferably carbendazim or 2-methoxycarbonylamino-benzimidazole, in either order.

BACKGROUND OF THE INVENTION

Cancers are a leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but unfortunately, many of these agents also destroy normal cells. Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. The exact mechanism for the action of these chemotherapeutic agents are not always known. Moreover, while some chemotherapeutic agents reduce the tumor mass significantly after one treatment, they unfortunately cannot be administered again to the same patient when the tumor returns as is usually the case. Some can only be administered once in a lifetime, others require several months or years delay between treatments.

Clearly, the development of materials that would target tumor cells due to some unique specificity for them would be a breakthrough. Alternatively, materials that were cytotoxic to tumor cells while exerting mild effects on normal cells would be desirable. It has been found that the benzimidazoles are especially effective in suppressing the growth of the cancers and tumors. The use of these benzimidazoles in sequential combination with other chemotherapeutic agents which are effective in debulking the tumor is a novel method of treatment. The preferred method involves first debulking or reducing the mass of the tumor with a cytotoxic agent and then administering the benzimidazoles.

It is an object of this invention to provide an anti-cancer therapy comprising a administering a chemotherapeutic agent first to reduce the mass of the tumor and then administering a benzimidazole derivative as defined herein to maintain or destroy the cancer. The agents may also be administered with the benzimidazole first and then the chemotherapeutic agent.

The bezimidazole can be administered in conjunction with a potentiator.

These and other objects will become evident from the following detailed description of this inventions.

SUMMARY OF THE INVENTION

A method of treating cancer in mammals, and in particular, warm blooded animals and humans, comprising administering a chemotherapeutic agent which significantly reduces the mass of the tumor or cancer, and then administering a safe and effective amount of a benzimidazole selected from the group consisting of:

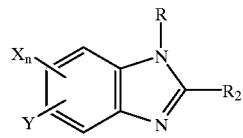

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen, or an alkyl group of from 1 to 8 carbon atoms or $CONHR_3$ and $R_3$ is alkyl of less than 7 carbons, preferably butyl or isobutyl, and $R_2$ is 4-thiazolyl, $NHCOOR_1$ wherein $R_1$ is aliphatic hydrocarbon of less than 7 carbon atoms, and preferably an alkyl group of less than 7 carbon atoms is claimed.

Preferably the compositions are:

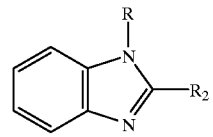

wherein R is hydrogen or $CONHR_3$ and $R_3$ is alkyl of less than 7 carbons, preferably butyl or isobutyl or an alkyl of 1 through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid addition salts with both organic and inorganic acids. The most preferred compounds are 2-(4-thiazolyl)benzimidazole, methyl-(butylcarbamoyl-2-benzimidazolecarbamate and 2-methoxycarbonylamino-benzimidazole and those wherein Y is chloro.

These compositions can be used to inhibit the growth of cancers and other tumors in humans or animals by administration of an effective amount either orally, rectally, topically or parenterally, intravenously or by injection into the tumor. Potentiators can also be used with this composition.

DETAILED DESCRIPTION OF THE INVENTION

A. Definitions

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the benzimidazoles and their derivatives with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle, including liposomes, for delivering the anti-cancer agent to the animal or human. The carrier may be liquid or solid and is selected with the planned manner of administration in mind.

As used herein, "cancer" refers to all types of cancers or neoplasm or malignant tumors found in mammals, including tumors and leukemia.

As used herein, the "benzimidazoles, and their salts" are described in detail below. Preferred materials are the products sold under the names "thiabendazole®", "benomyl®" and "carbendazim®" by BASF and Hoechst, DuPont and MSD-AgVet.

As used herein "chemotherapeutic agents" includes DNA-interactive Agents, Antimetabolites, Tubulin-Interactive Agents, Hormonal agents and others, such as Asparaginase or hydroxyurea.

As used herein "potentiators" are materials such as triprolidine and its cis-isomer and procodazole which are used in combination with the chemotherapeutic agents and benzimidazoles.

As used herein "significantly reduce" means to reduce the mass of the tumor by significant amount. This will usually be to less than 50% of its original mass, and preferably to reduce the mass to non-detectable amounts.

B. The Benzimidazole Compounds

The benzimidazole derivatives are known for their antifungal activities. Surprisingly it has been found that these compounds can also cause apoptosis in cancer cell lines. Apoptosis is specific cell death which differs from necrosis. Most cancer cells can live indefinitely; cancer cells are often referred to as immortalized cell lines. Therefore the ability to induce apoptosis is very important.

The compounds have the following structure:

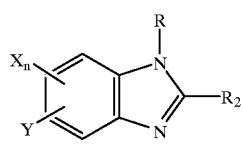

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen, $CONHR_3$ and $R_3$ is alkyl of less than 7 carbons, preferably butyl or isobutyl or an alkyl group having from 1 to 8 carbons, and $R_2$ is 4-thiazolyl, $NHCOOR_1$ wherein $R_1$ is aliphatic hydrocarbon of less than 7 carbon atoms, and preferably and alkyl group of less than 7 carbon atoms. Preferably the compositions are:

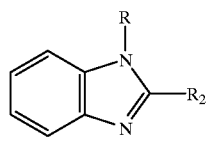

wherein R is hydrogen, $CONHR_3$ and $R_3$ is alkyl of less than 7 carbons, preferably butyl or isobutyl or an alkyl of 1 through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid addition salts with both organic and inorganic acids.

The most preferred compounds are 2-(4-thiazolyl)benzimidazole, methyl-(butylcarbamoyl)-2-benzimidazolecarbamate and 2-methoxycarbonylaminobenzimidazole and the compounds wherein Y is chloro and X is hydrogen.

These compounds are prepared according to the method described in U.S. Pat. No. 3,738,995 issued to Adams et al, Jun. 12, 1973. The thiazolyl derivatives are prepared according to the method described in Brown et al., *J. Am. Chem. Soc.*, 83, 1764 (1961) and Grenda et al., *J. Org. Chem.*, 30, 259 (1965).

C. Chemotherapeutic Agents

The chemotherapeutic agents are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in the sequential method in combination benzimidazoles primarily include members of the DNA-interactive Agents, Antimetabolites, Tubulin-Interactive Agents groups. For a detailed discussion of the chemotherapeutic agents and their method of administration, see Dorr, et al, *Cancer Chemotherapy Handbook*, 2d edition, pages 15–34, Appleton & Lange (Connecticut, 1994) herein incorporated by reference.

In order to reduce the mass of the tumor or stop the growth of the cancer cells, the chemotherapeutic agent must prevent the cells from replicating and also must interfere with the cell's ability to maintain itself. The agents which do this are primarily the DNA-interactive agents such as Cisplatin, and tubulin interactive agents.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plicamycin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

aziridines such as Thiotepa;

methanesulfonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:

Intercalators, such as Amsacrine, Dactinomycin, Daunorubicin, Doxorubicin, Idarubicin, and Mitoxantrone;

nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficienty like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin;

sugar modified analogs include Cyctrabine, Fludarabine;

ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin interactive agents include Vincristine and Vinblastine, both alkaloids and Paclitaxel.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prodnisolone.

Hydroxyurea appears to act primarily through inhibition of the enzyme ribonucleotide reductase.

Asparagenase is an enzyme which converts asparagine to nonfunctional aspartic acid and thus blocks protein synthesis in the tumor.

The hormonal agents and leutinizing hormones are not usually used to substantially reduce the tumor mass. However, they can be used in conjunction with the chemotherapuetic agents or the benzimidazoles.

Hormonal blocking agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlorotrianisene and Idenestrol;

progestins such as Hydroxyprogesterone caproate, Medroxyprogesterone, and Megestrol;

androgens such as testosterone, testosterone propionate; fluoxymesterone, methyltestosterone;

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamosifen, antiandrogen agents such as Flutamide; and antiadrenal agents such as Mitotane and Aminoglutethimide.

D. Potentiators

The "potentiators" can be any material which improves or increases the efficacy of the pharmaceutical composition and/or act on the immune system. One such potentiator is triprolidine and its cis-isomer which are used in combination with the chemotherapeutic agents and the benzimidazole. Triprolidine is described in U.S. Pat. No. 5,114,951 (1992). Another potentiator is procodazole, 1H-Benzimidazole-2-propanoic acid; [β-(2-benzimidazole) propionic acid; 2-(2-carboxyethyl)benzimidazole; propazol) Procodazole is a non-specific active immunoprotective agent against viral and bacterial infections and can be used with the compositions claimed herein.

The potentiators can improve the efficacy of the benzimidazole compounds and can be used in a safe and effective amount. These combinations can be administered to the patient or animal by oral, rectal, topical or parenteral administration.

Antioxidant vitamins such as ascorbic acid, beta-carotene, vitamin A and vitamin E can be administered with the compositions of this invention.

E. Dosage

Any suitable dosage can be given in the method of the invention. The type of compounds and the carriers and the amount will vary widely depending on the species of the warm blooded animal or human, body weight, and cancer, or tumor being treated. The range and ratio of the chemotherapeutic agent and benzimidazoles and their derivatives used will depend on the type of chemotherapeutic agent and the cancer being treated. Generally, for the benzimidazoles a dosage of between about 2 milligrams (mg) per kilogram (kg) of body weight and about 4000 mg per kg of body weight is suitable. Higher dosages, up to 6000 mg/kg can also be used. Preferably from 15 mg to about 3000 mg/kg of body weight is used for the benzimidazoles. For the chemotherapeutic agents, a lower dosage may be appropriate, i.e., from about 0.01 mg/kg of body weight to about 400 mg/kg body weight, although amounts up to 1500 mg/lkg can be used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules, liposomes and the like or in liquid form suitable for oral, rectal, topical, intravenous injection or parenteral administration or injection into or around the tumor.

F. Dosage Delivery Forms

The benzimidazoles and their derivatives and chemotherapeutic agents are typically mixed with a pharmaceutically acceptable carrier. This carrier can be a solid or liquid or a liposome and the type is generally chosen based on the type of administration being used. The active agent can be coadministered in the form of a tablet or capsule, liposome, or as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms; Tablets* (1981); and Ansel, *Introduction to Pharmaceutical Dosage Forms 2nd Edition* (1976).

G. Method of Treatment

The method of treatment can be any suitable method which is effective in the treatment of the particular cancer or tumor type that is being treated. Treatment may be oral, real, topical, parenteral or intravenous administration or by injection into the tumor and the like. The method of applying an effective amount also varies depending on the tumor being treated. It is believed that parenteral treatment by intravenous, subcutaneous, or intramuscular application of the benzimidazole compounds, formulated with an appropriate carrier, additional cancer inhibiting compound or compounds or diluent to facilitate application will be the preferred method of administering the compounds to warm blooded animals.

Preferably, the chemotherapuetic agent is administered first to significantly reduce the size of the cancer or tumor mass. Usually this will take 3 to about 14 days. The reduction in the tumor or level of cancer cells will be to less than 50% of the original level. Radiation therapy may be used in conjunction with the chemotherapuetic treatment.

Once the tumor has been reduced, the benzimidazole is administered. Because of the relative safety of this material, it can be administered for from 14 days to 365 days as needed to maintain its effectiveness in reducing the regrowth of the cancer.

The following example is illustrative and are not meant to be limiting to the invention.

EXAMPLE 1

In a mouse model for breast cancer cytoxan is administered to the animal reduce the tumor mass significantly. Carbendazim is administered to the mice at 4000, 5000, and 6000 mg/kg of body weight in a separate leg. The tumor continued to decrease in size and its regrowth was limited even after 180 days with the carbendazim treatment. The growth was dose dependent. The cytoxan treated control had tumor regrowth after 100 days; and when stimulated with estrogen at day 115 had a rapid regrowth. Even with estrogen stimulation, the carbendazim treated animals had no significant change in tumor mass. After 130 days, carbendazim to the mice (at 4000, 5000, and 6000 mg/kg of body weight) that had been treated with cytoxan. The tumor continued to decrease in size and its regrowth was limited even after 180 days.

What is claimed is:

1. A method of treating cancer sensitive to the combination below in warm blooded mammals comprising the steps of:

a) administering to said mammal a safe and effective amount of a chemotherapeutic agent, wherein said chemotherapeutic agent is a DNA-interactive agent, for a time sufficient to reduce the cancer significantly; and b) then administering to said mammal a pharmaceutical composition comprising
      (i) a safe and enhanced amount of a benzimidazole of the formula:

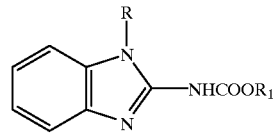

or a pharmaceutically acceptable organic or inorganic acid addition salt thereof, wherein:
   R is hydrogen, an alkyl group of from 1 to 8 carbon atoms, or $CONHR_3$ wherein $R_3$ is alkyl of less than 7 carbons; and
   $R_1$ is methyl, ethyl, or isopropyl; and
      (ii) an amount of a potentiator that enhances efficacy of said benzimidazole.

2. A method of treating cancer in warm blooded mammals according to claim 1 wherein said benzimidazole is selected from the group consisting of methyl 1-(butylcarbamoyl)-2-benzimidazolecarbamate and 2-methoxycarbonylaminobenzimidazole.

3. A method according to claim 2 wherein from about 2 mg/kg body weight to about 4000 mg/kg of said benzimidazole is administered.

4. A method according to claim 1 wherein from about 150 mg/kg body weight to about 4000 mg/kg body weight of said benzimidazole is administered and from about 0.5 mg/kg body weight to about 400 mg/kg body weight of said chemotherapeutic agent is administered.

5. A method according to claim 4 wherein said benzimidazole is administered in a liquid form selected from the group consisting of an aqueous solution, an alcohol solution, an emulsion, a suspension, a suspension reconstituted from non-effervescent or effervescent preparations, and a suspension in pharmaceutically acceptable fats or oils.

6. A method according to claim 1 wherein said chemotherapeutic agent is cyclophosphamide, said benzimidazole is 2-(methoxycarbonylamino)benzimidazole, and said potentiator is triprolidine or its cis-isomer.

7. A method according to claim 1 wherein said pharmaceutically acceptable salt is a chloride salt.

8. A method according to claim 1 wherein said potentiator is triprolidine or the cis-isomer of triprolidine.

9. A method of treating breast cancer in warm blooded mammals comprising administering a safe and effective amount of a chemotherapeutic agent selected from the group consisting of cyclophosphamide for a time sufficient to reduce the cancer significantly, and then administering a pharmaceutical composition comprising (i) a safe and enhanced amount of 2-(methoxycarbonylamino) benzimidazole or a pharmaceutically acceptable organic or inorganic acid addition salt thereof and (ii) an amount of a potentiator that enhances efficacy of said 2-(methoxycarbonylamino)benzimidazole.

10. A method according to claim 9 wherein said chemotherapuetic agent is administered for from about 3 to 14 days.

11. A method according to claim 10 wherein said 2-methoxycarbonylamino-benzimidazole is administered for from about 3 days to about 365 days.

12. A method according to claim 9 wherein said potentiator is triprolidine or the cis-isomer of triprolidine.

* * * * *